United States Patent [19]
Kandel

[11] Patent Number: 5,326,357
[45] Date of Patent: Jul. 5, 1994

[54] RECONSTITUTED CARTRIDGE TISSUE

[75] Inventor: Rita A. Kandel, Toronto, Canada

[73] Assignee: Mount Sinai Hospital Corporation, Toronto, Canada

[21] Appl. No.: 835,831

[22] Filed: Mar. 18, 1992

[51] Int. Cl.$^5$ .......................... A61F 2/28; A61F 2/02; A61F 13/00; C12N 5/00
[52] U.S. Cl. ........................................ 623/16; 623/11; 424/422; 424/423; 435/240.23
[58] Field of Search ...................... 623/11, 13, 16, 18, 623/66; 424/422, 423; 128/DIG. 8; 435/240.1, 240.23, 240.243

[56] References Cited

U.S. PATENT DOCUMENTS

| | | | |
|---|---|---|---|
| 3,703,575 | 11/1972 | Kiel | 424/423 |
| 4,356,261 | 10/1982 | Kuettner . | |
| 4,642,120 | 2/1987 | Nevo et al. | 623/11 X |
| 4,757,017 | 6/1988 | Cheung . | |
| 4,846,835 | 7/1989 | Grande | 623/11 |
| 4,904,259 | 2/1990 | Itay . | |
| 4,996,154 | 2/1991 | Gabriels, Jr. | 435/240.241 |
| 5,037,656 | 8/1991 | Pitt et al. | 424/443 |
| 5,041,138 | 8/1991 | Vacanti et al. | 623/16 |
| 5,053,050 | 1/1991 | Itay | 623/16 |

FOREIGN PATENT DOCUMENTS

| | | |
|---|---|---|
| 0175286A3 | 3/1986 | European Pat. Off. . |
| 0396138A2 | 11/1990 | European Pat. Off. . |
| WO90/12603 | of 1990 | PCT Int'l Appl. . |

OTHER PUBLICATIONS

Urist, Marshall R., "Clinical Orthopaedics and Related Research", No. 186, Jun. 1984, Philadelphia, Pa., U.S., pp. 231–239, T. Kimura et al., Chondrocytes Embedded in Collagen Gels Maintain Cartilage Phenstype During Long Term Cultures.
Aydelotte and Kuettner, Conn. Tiss. Res., 18:205, 1988.
Zanetti et al., J. Cell Biol., 101:53, 1985.
Poole et al., J. Anat., 138:13, 1984.
Urban and Bayliss, Biochem. Biophys. Acta., 992:59, 1988.
Brown et al., Conn. Tiss. Res., 24:157, 1990.
Schneiderman et al., J. Orthop. Res., 4:393, 1986.
Lane and Brighton, Arth. Rheum., 17:235, 1974.
Morales et al., J. Biol. Chem., 259:6720, 1984.
Manning and Bonner, Arth. Rheum., 10:235, 1967.
Horwitz and Dorfman, J. Cell Biol., 45:434, 1970.
Green, Clin. Orthop. Rel. Res., 75:248, 1971.
Von der Mark et al., Nature, 267:531, 1977.
Solursh, Am. J. Med. Gen., 34:30, 1989.
Watt and Dudhia, Differentiation, 38:140, 1988.
Van Kampen and Veldhuijzen, Exp. Cell. Res., 140:440, 1982.
Delbruck et al., Conn. Tiss. Res., 15:155, 1986.
Thompson et al., Exp. Cell. Res., 157:483, 1985.
Bassleer et al., In Vitro, 22:113, 1986.
Cheung, In Vitro Cell. Dev. Biol., 21:353, 1985.
Guo et al., Conn. Tiss. Res., 19:277, 1989.
Aulthouse et al., In Vitro Cell & Dev. Biol., 25:659, 1989.
Solursh, J. Cell. Biochem., 45:258, 1991.
O'Driscoll et al., Trans. Orthop. Res., 37:125, 1991.
Nakahara et al., Bone, 11:181, 1990.
Amiel et al., Conn. Tiss. Res., 18:27, 1988.
Kuettner et al., (J. Cell. Biol.), 93:751,. (1982).
Macklis et al., In Vitro Cell. Develop. Biol., 21:180, 1985.
Kandel et al., Biochem. Biophys. Acta., 1035:130, 1990.
Streuli and Bissell, J. Cell. Biol., 110:1405, 1990.
Buck and Horwitz, Ann. Rev. Cell Biol., 3:179, 1987.
Goldberg and Kolibas, Conn. Tissue Res., 24:265, 1990.
Yannas, Collagen, 3:87.
Kato et al., Proc. Natl. Acad. Sci., 85:9552, 1988.
Benya & Shaffer, Cell., 30:215, 1982.

(List continued on next page.)

*Primary Examiner*—Randall L. Green
*Assistant Examiner*—Dinh X. Nguyen
*Attorney, Agent, or Firm*—Bereskin & Parr

[57] ABSTRACT

The present invention relates to cartilage tissue reconstituted on a substrate; to a method for producing reconstituted cartilage tissue; and to cartilage tissue reconstituted in vitro from isolated chondrocytes cultured on a substrate.

22 Claims, 8 Drawing Sheets

OTHER PUBLICATIONS

Franzen et al., Differentiation, 36:199, 1987.
Solursh, Development and Diseases of Cartridge and Bone Marrow, Alan R. Liss Inc., 1987.
Billings et al., Acta. Orthop. Scand., 61:201, 1990.
Schwartz et al., In Vitro, 18:254, 1982.
Jennings et al., Cell. Biol. Int. Rep., 7:149, 1983.
Hale et al., In Vitro Cell. Biol. & Dev. Biol., 22:597, 1986.
Trippel et al., J. Bone & Joint Surgery, 1990:816.
Robinson et al., Calcif. Tissue Int., 46:246, 1990.

Type I          Type II

RECONSTITUTED CARTRIDGE TISSUE

FIELD OF THE INVENTION

The present invention relates to reconstituted cartilage tissue; to a method for producing reconstituted cartilage tissue; and to cartilage tissue reconstituted in vitro from isolated chondrocytes.

BACKGROUND OF THE INVENTION

Articular cartilage is a specialized tissue found at the end of articulating bones. Cartilage, unlike other connective tissues, lacks blood vessels, nerves, lymphatics and basement membrane. It is responsible for the distribution of load resistance to compressive forces, and the smooth gliding that is part of joint function.

Cartilage is composed of chondrocytes which synthesize an abundant extracellular matrix, which is composed of water, collagens, proteoglycans and noncollagenous proteins and lipids. Collagen serves to trap proteoglycans and to provide tensile strength to the tissue. Type II collagen is the predominant collagen in cartilage tissue. The proteoglycans are composed of a variable number of glycosaminoglycan chains, keratan sulphate, chondroitin sulphate and/or dermatan sulphate, and N-linked and O-linked oligosaccharides covalently bound to a protein core. The sulphated glycosaminoglycans are negatively charged resulting in an osmotic swelling pressure that draws in water.

Although, histologically, articular cartilage appears very homogenous, the matrix organization and composition differ from the superficial to the deep zones (Aydelotte and Kuettner, Conn. Tiss. Res. 18: 205, 1988; Zanetti et al, J. Cell Biol. 101: 53, 1985; and Poole et al, J. Anat. 138: 13, 1984). Articular cartilage appears to be composed of zones which show a characteristic gradation of features from the surface of the tissue to the base of the tissue adjacent to the bone. In the superficial zone, for example, chondrocytes are flattened and lie parallel to the surface embedded in a matrix that contains tangentially arranged collagen and few proteoglycans. In the mid zone, chondrocytes are spherical and surrounded by a matrix rich in proteoglycans and obliquely organized collagen fibers. In the deep zone, close to the bone, the collagen fibers are vertically oriented. The keratan sulphate rich proteoglycans increase in concentration with increasing distance from the cartilage surface (Zanetti et al, supra).

Ultrastructural variation is evident between the pericellular and interterritorial matrix areas. The pericellular collagen fibers are much thinner and do not exhibit the usual 68 nm periodicity characteristic of collagen in the interterritorial zone. It is not known how these zones are established or maintained (Poole et al, supra: Urban and Bayliss, Biochem. Biophys. Acta. 992: 59, 1989; Brown et al, Conn. Tiss. Res. 24: 157, 1990; Schneiderman et al J. Orthop. Res. 4: 393, 1986).

Studies of cartilage organization and pathophysiology have been severely restricted by the limited availability of cartilage tissue and the inability of in vitro culture systems to mimic the organization of in vivo cartilage tissue. In vivo cartilage has been removed and maintained in explant cultures, but there are several problems associated with these cultures (Poole et al supra Lane and Brighton, Arth. Rheum 17: 235, 1974; and Morales et al, J. Biol. Chem. 259: 6720, 1984). There is a loss of matrix molecules from the cartilage during culture, and the amount of cartilage available for experimentation is therefore limited. Chondrocytes have been isolated from cartilage and grown in monolayer culture systems (Manning and Bonner, Arth. Rheum. 10: 235, 1967; Horwitz and Dorfman, J. Cell Biol. 45: 434, 1970; and Green, Clin. Orthop. Rel. Res. 75: 248, 1971). However, chondrocyte phenotype in these cultures is labile and the chondrocytes dedifferentiate to fibroblasts, as defined by production of type I collagen and small nonaggregating proteoglycans (Von der Mark et al, Nature 267: 531, 1977; and Solursh, Am. J. Med. Gen. 34: 30, 1989).

Maintaining chondrocytes in a spherical shape has been shown to slow down or prevent dedifferentiation of the chondrocyte phenotype (Watt and Dudhia, Differentiation 140, 1988). Accordingly, culture systems have been developed to maintain the cells in a spherical shape. Primary cell cultures either plated at high density in monolayer or droplet form, in suspension culture, in collagen gel, in or on agarose gel, in composition agarose-collagen gels, in alginate or on apatite beads, or a combination of monolayer culture followed by transfer to agarose culture have been employed in an attempt to slow down or prevent dedifferentiation (Kuettner et al, J. Cell. Biol. 93: 743, 1982; Van Kampen and Veldhuijzen, Exp. Cell. Res. 140: 440, 1982; Delbruck et al, Conn. Tiss. Res. 15: 155, 1986; Thompson et al, Exp. Cell. Res. 157: 483, 1985; Bassler et al, In Vitro 22: 113, 1986; Cheung, In Vitro Cell. Dev. Biol. 21: 353, 1985; Guo et al, Conn. Tiss. Res. 19: 277, 1989; Aulthouse et al, In Vitro 25: 659, 1989; and Solursh, J. Cell. Biochem. 45: 258, 1991).

Alternative approaches to maintaining the chondrocyte phenotype have been to induce chondrogenesis by growing mesenchymal cells in diffusion chambers or in monolayer in the presence of beta TGF (O'Driscoll et al, Trans. Orthop. Res. 37: 125, 1991 and Nakahara et al, Bone 11: 181, 1990), or perichondrial grafts (Amiel et al, Conn. Tiss. Res. 18: 27, 1988). Under all of the above conditions the chondrocytes maintain at least a partial chondrocyte phenotype, as indicated by the synthesis of type II collagen and proteoglycans specific to articular cartilage. However, there are a number of problems with these types of cultures. Proliferation in some of the cultures is inhibited so that only a limited number of cells can be generated. It has also proved difficult to isolate cells from these cultures. The most important limitation, however, is that none of these culture systems can mimic the in vivo morphology of articular cartilage, including the cellular and matrix organization described above.

Green (Clin. Orth. Rel. Res. 75:248. 1971) teaches a process for growing chondrocytes in vitro in pelleted aggregate cultures on Millipore cellulose acetate inserts. Green describes the in vitro production of a chondro-myxoid matrix by rabbit chondrocytes. Kuettner et al (J. Cell. Biol. 93:751, (1982)) describe methods of culturing bovine chondrocytes on plastic dishes. Kuettner in U.S. Pat. No. 4,356,261 describes methods of culturing chondrocytes in suspension culture in roller bottles. Type II collagen was reported as being the major matrix-associated collagen synthesized in vitro. Kuettner et al analyzed proteoglycans synthesized by the chondrocytes in their culture system by chromatography of $^{35}S$ pulse-labelled cultures. The proteoglycans synthesized were compared with those of in vivo bovine articular cartilage. Bassler et al (1986) teach a suspension culture of human chondrocytes wherein aggregates of chondrocytes with secreted matrix were produced by a gyratory shaker. Type II collagen and proteoglycans were detected in the secreted matrix by immunofluoresence and radioimmunoassay.

Cheung (In Vitro Cell. Dev. Biol. 21:353, 1985) teaches a method of culturing canine chondrocytes on porous hydroxyapatite ceramic granules. The cells reportedly proliferated and secreted metachromatic extracellular matrix for up to 13 months. An agarose gel matrix has also been described as suitable for the in vitro culture of human chondrocytes (Delbruck et al, Conn. Tiss. Res. 15:155, 1986). Delbruck et al disclosed human chondrocytes distributed in the agarose and forming a pericellular region surrounded by an interterritorial-like region. Type II collagen was detected in the gel matrix cultures by immunofluoresence and acid soluble collagens were examined by SDS polyacrylamide gel electrophoresis.

Watt and Dudhia (Differentiation 38:140, 1988) disclose a composite gel of collagen and agarose for the culture of porcine chondrocytes. The composite gel prevented chondrocytes spreading. However, virtually no extracellular matrix was secreted in the low density culture composite gels.

Macklis et al (In Vitro Cell. Develop. Biol. 21:180, 1985) teach a collagen surface for culturing peripheral nervous system cells, comprising collagen derivatized to polystyrene plastic culture dishes. Macklis et al disclose that the derivatized coating process yielded enhanced collagen adhesion and increased long term survival of cultured nerve cells, compared to collagen coating produced by absorption techniques.

SUMMARY OF THE INVENTION

The present inventor has reconstituted cartilage tissue on a substrate in vitro from isolated chondrocytes. The reconstituted cartilage tissue has a biochemical composition and physiological organization substantially the same as animal articular cartilage tissue. In particular, the present inventor reconstituted cartilage characterized by a continuous layer of cartilage tissue having a substantial extracellular matrix and possessing zones very similar to those found in bovine cartilage in vivo. The superficial zone is characterized by chondrocytes which are flattened and arranged parallel to the substrate, and a matrix which contains collagen fibres. Mid and deep zones have spherical chondrocytes and the matrix contains collagen fibres. The reconstituted cartilage tissue ultrastructurally has a pericellular and interterritorial arrangement similar to that of in vivo bovine cartilage.

The reconstituted cartilage of the present invention also has a biochemical composition substantially the same as animal articular cartilage. In particular, type II collagen is present throughout the reconstituted cartilage and the ratio of galactosamine to glucosamine amino sugars in the glycosaminoglycans in the reconstituted cartilage tissue of the invention is between about 4.5 and 6.5. The reconstituted cartilage tissue of the invention also responds to interleukin 1 $\beta$ in a similar manner to in vivo cartilage tissue.

Broadly stated the invention relates to cartilage tissue reconstituted on a substrate in vitro from isolated chondrocytes, said tissue having a biochemical composition and physiological organization substantially the same as animal articular cartilage tissue.

The invention also relates to a method for producing reconstituted cartilage tissue comprising removing articular cartilage tissue from the joint of an animal; digesting said cartilage tissue to obtain isolated chondrocytes; forming a monolayer of chondrocytes on a substrate; culturing the chondrocytes in growth media to produce a tissue having a biochemical composition and physiological organization substantially the same as articular cartilage tissue.

The invention further relates to artificial cartilage tissue reconstituted in vitro by digesting cartilage tissue to obtain isolated chondrocytes; forming a monolayer of chondrocytes on a substrate; culturing the chondrocytes and growth medium to produce a tissue having a biochemical composition and physiological organization substantially the same as articular cartilage tissue.

The invention still further relates to a method of using the reconstituted cartilage tissue of the present invention to test pharmaceutical preparations for efficacy in the treatment of diseases of the joint and to a method of using the reconstituted tissue of the present invention as an implant to replace or repair damaged or deficient cartilage.

DETAILED DESCRIPTION OF THE INVENTION

As hereinbefore mentioned, the present invention provides cartilage tissue reconstituted on a substrate in vitro from isolated chondrocytes, said tissue having a biochemical composition and physiological organization substantially the same as animal articular cartilage tissue.

The reconstituted cartilage tissue of the invention is characterized by a continuous layer of cartilage tissue, having a substantial extracellular matrix, and comprising a superficial zone wherein the chondrocytes are flattened and arranged parallel to the substrate, and mid and deep zones wherein the chondrocytes are spherical and wherein the matrix in the superficial, mid and deep zones contains collagen fibers.

The present invention also relates to a method for producing reconstituted cartilage tissue. The method comprises removing articular cartilage from the joint of an animal; digesting the cartilage tissue to obtain isolated chondrocytes; forming a monolayer of chondrocytes on a substrate; and culturing the chondrocytes in growth media to produce a tissue having a biochemical composition and physiological organization substantially the same as articular cartilage tissue.

The reconstituted cartilage tissue of the present invention may be prepared from chondrocytes isolated from articular cartilage from animals, preferably humans. A particularly useful system may be prepared from chondrocytes isolated from bovine articular cartilage, for example from the metacarpophalangeal joints.

The chondrocytes may be isolated by sequential enzyme digestion techniques, such as those described in Kandel et al, Biochem. Biophys. Acta. 1035:130, 1990. For example, the cartilage may be treated with 0.5% protease followed by 0.04% bacterial collagenase. The chondrocytes are plated on a substrate preferably a porous tissue culture insert, for example a MILLICELL ®-CM insert, which has been coated with an attachment factor. Attachment factors are known in the art, see for example, Streuli and Bissell, J. Cell. Biol. 110:1405, 1990 and Buck and Horwitz, Ann, Rev. Cell Biol. 3:179, 1987. Examples of attachment factors include type I collagen, type II collagen, type IV collagen, fibronectin, gelatin, laminin, polylysine, vitronectin, cytotactin, echinonectin, entactin, tenascin, thrombospondin, uvomorulin, biglycan, chondroitin sulfate, decorin, dermatan sulfate, heparin, and hyaluronic acid. Preferably, the attachment factor used in the method of the invention is collagen, most preferably type I collagen. The chondrocytes are plated at a high cell density of at least 0.1 cm$^2$, preferably from 1.0 to $7 \times 10^6$ cm$^2$.

In a preferred embodiment of the invention the substrate is a MILLICELL ®-CM tissue culture insert, pore size 0.4µm, coated with a growth attachment factor, preferably collagen, most preferably type I collagen diluted in acetic acid. The insert may subsequently be air dried and sterilized, for example by ultra violet light.

The chondrocytes seeded on the coated substrate, may be grown in suitable culture conditions. Examples of suitable culture media are known in the art, such as Ham's F12 medium. The culture medium may contain serum, for example fetal bovine serum in a concentration range of about 2–15% and may further contain growth factors and ascorbic acid. The cells may be cultured at 37° C. in a humidified atmosphere supplemented with $CO_2$, for at least 2 weeks.

The present inventor has found that, after as little as 14 days in culture, the cells will produce a tissue with substantial extracellular matrix, which is substantially identical to in vivo bovine cartilage. The cells produce a substantial extracellular matrix and form a continuous layer of cartilage tissue possessing zones very similar to those found in natural bovine cartilage in vivo. The superficial zone is characterized by chondrocytes having a flattened morphology and a matrix which does not stain, or stains poorly, with toluidine blue, indicating the relative absence of sulphated proteoglycans. Chondrocytes in the mid and deep zones have a spherical appearance and the matrix contains abundant sulphated proteoglycans, as evidenced by staining with toluidine blue. Collagen fibers are present diffusely throughout the matrix.

The reconstituted cartilage tissue ultrastructurally has a pericellular and interterritorial arrangement similar to that of in vivo bovine cartilage. The chondrocytes possess abundant rough endoplasmic reticulum and are surrounded by matrix. The pericellular matrix contains numerous thin non-banded collagen fibers. The collagen in the interterritorial matrix is less compacted and embedded in electron translucent amorphous material, similar to articular cartilage. Collagen fibers in the interterritorial region of the matrix exhibit the periodic banding characteristic of collagen fibers in the interterritorial zone of cartilage tissue.

The biochemical composition of the reconstituted cartilage tissue is substantially the same as animal articular cartilage tissue. For example, the presence of type II collagen in the reconstituted cartilage tissue is indicative of the differentiated phenotype of chondrocytes. The presence of type II collagen was determined in the reconstituted cartilage tissue by means of polyacrylamide gel electrophoresis and Western blot analysis. Type II collagen is present throughout the reconstituted cartilage tissue as determined by immunohistochemical staining of the cartilage using polyclonal antibody directed against Type II collagen. The ratio of galactosamine to glucosamine amino sugars found in the glycosaminoglycans present in cartilage in the reconstituted cartilage tissue of the present invention is between about 4.5 and 6.5.

The reconstituted cartilage tissue responds to interleukin 1β in a similar manner to in vivo cartilage tissue. Interleukin 1β stimulates production of matrix metalloproteases that can degrade cartilage matrix macromolecules and inhibit synthesis of proteoglycans. Treatment of the reconstituted tissue with human recombinant interleukin 1β results in a loss of cartilage and matrix components.

The reconstituted cartilage tissue of the present invention can be used as a model system for in vitro studies of cartilage structure, function and development. In particular, the reconstituted cartilage of the present invention may be used in the testing of pharmaceutical preparations useful in the treatment of diseases of the joint, for example osteoarthritis, inflammatory arthropathies, septic arthritis and crystalline arthropathies. The reconstituted cartilage tissue of the invention may also be implanted into the joints of patients to replace or repair damaged or deficient cartilage. In addition the cartilage can be used to test angiogenic factors as the cartilage is normally resistant to vascular infiltration. It is also contemplated that the reconstituted cartilage tissue of the present invention can be used to enhance healing of bone fractures when inserted into the site of a fracture.

The following non-limiting examples are illustrative of the present invention:

EXAMPLE 1

Reconstituting Cartilage Tissue in Vitro

Chondrocytes were isolated from bovine articular cartilage obtained from metacarpophalangeal joints using the sequential enzyme digestion techniques described in Kandel et al, Biochem. Biophys. Acta. 1053:130 (1990). Briefly, the cartilage was treated with 0.5% protease for one hour and 0.04% bacterial collagenase overnight. The isolated chondrocytes were washed three times and plated at a cell density of approximately 1.5×10⁶/cm² on collagen-coated MIL-LICELL ®-CM porous tissue culture inserts.

To prepare the collagen-coated inserts, MIL-LICELL ®-CM inserts, pore size 0.4 μm, were coated with Type I collagen (Vitrogen, Type I collagen, Collagen Corporation), diluted to 1 mg/ml with 12 mM acetic acid. Following coating, the inserts were air dried for up to 18 hours and sterilized with ultraviolet light for 15 minutes.

The collagen-coated inserts, seeded with chondrocytes, were placed in sterile tissue culture wells and cultured in Ham's F12 medium, supplemented with 5% fetal bovine serum. The cells were cultured at 37° C. in a humidified atmosphere supplemented with 5% $CO_2$. The medium was changed 2.5 to 3 days after the initial plating and every 2 days thereafter. The volume of medium added depended on the size of inserts used. For the larger inserts (30 mm) 1.5 ml of medium was placed on top of the insert and 1.0 ml was placed underneath. The inserts were harvested at selected time intervals up until 3 months, fixed and examined by light or electron microscopy.

For light microscopy, the inserts were fixed in 10% formalin, embedded in paraffin and cut into sections approximately 5 μm thick. The sections were stained with either hematoxylin and eosin to visualize the cells or with the cationic dye, toluidine blue, to stain sulphated proteoglycans. In vivo samples of intact cartilage from bovine metacarpophalangeal joints were similarly processed for light microscopy.

For electron microscopy, representative portions of the insert culture were fixed in 2% glutaraldehyde for one hour at room temperature. The inserts were washed with phosphate buffer and then immersed in 1% osmium tetraoxide for one hour at room temperature. The inserts were washed with a phosphate buffer and dehydrated in graded ethanols to 100% ethanol. The inserts were immersed in 100% propylene oxide for 20 minutes, then embedded in plastic resin (SPURR ®) and polymerized overnight at 70° C. Thin sections were cut and stained with uranyl acetate and lead citrate before examination by electron microscopy.

Figure 2:
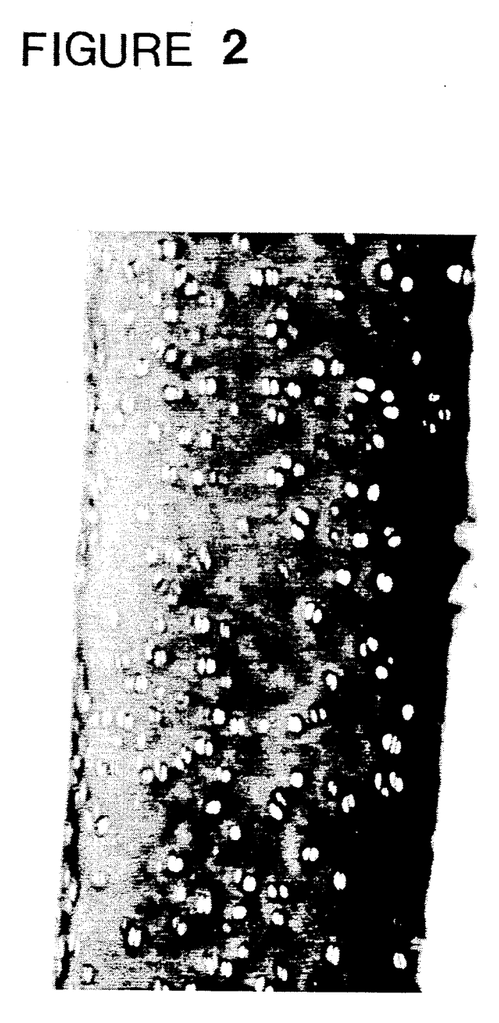
FIG. 2 is a photomicrograph showing cartilage from the bovine joint.
Figure 3:
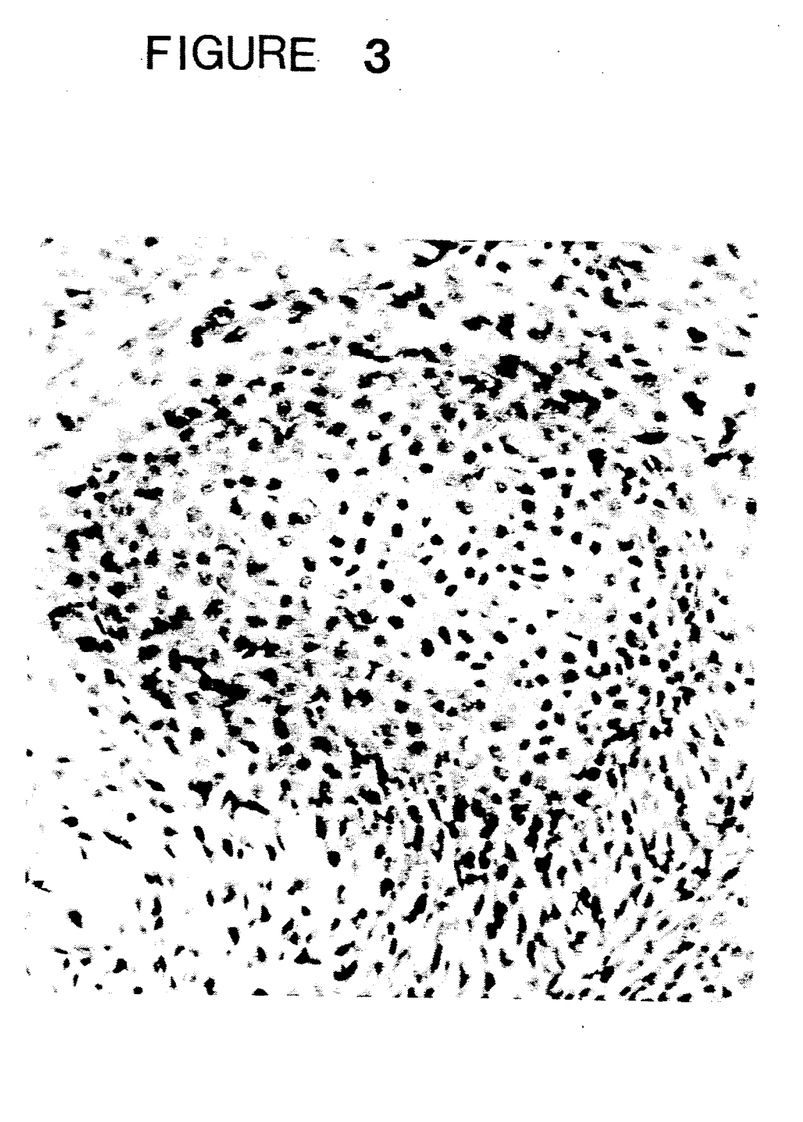
FIG. 3 is a photomicrograph of fetal cartilage showing the lack of cellular organization characteristic of articular cartilage (C)

After 2 weeks in culture the cells had produced a tissue with abundant extracellular matrix which was substantially identical to bovine cartilage in vivo. Morphological comparisons were made between the cartilage tissue produced by in vitro culture, shown in FIG. 1 and the in vivo cartilage tissue from the bovine joint, known in the art, shown in FIG. 2. FIG. 2 shows the organization of chondrocytes in cartilage tissue dissected from the bovine joint. The chondrocytes in the superficial regions are flattened and the chondrocytes in the deep layers are more spherical. Toluidine blue staining shows the presence of sulphated proteoglycans throughout the cartilage. The staining is lighter in the superficial zone suggesting there are fewer proteoglycans present. Fetal cartilage has no specific cellular organization as is shown in FIG. 3.

Figure 1:
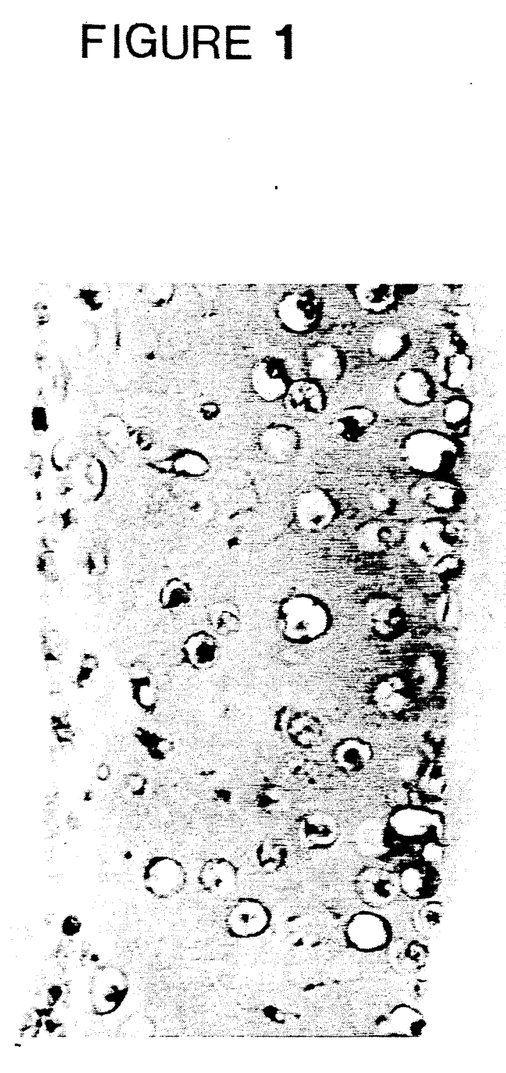
FIG. 1 is a photomicrograph showing cartilage generated by chondrocytes cultured on collagen-coated inserts (F) and stained with Toluidine blue.

The cartilage tissue grown in vitro, and shown in FIG. 1, was found to closely resemble in vivo bovine articular cartilage. Examination of 4 week old cultures by light microscopy showed that the cells had produced abundant extracellular matrix and formed a continuous layer of cartilage tissue possessing zones very similar to those found in natural bovine cartilage in vivo. The superficial zone was characterized by chondrocytes having a flattened morphology and a matrix which did not stain with toluidine blue, indicating the relative absence of sulphated proteoglycans. Chondrocytes in the mid zone had a less flattened appearance and the matrix contained sulphated proteoglycans, as evidenced by the metachromasia produced by toluidine blue staining. Chondrocytes in the deep zone were spherical in appearance and the matrix was metachromatic. Examination by polarized light microscopy showed the birefringence, indicative of collagen fibers.

Figure 4:
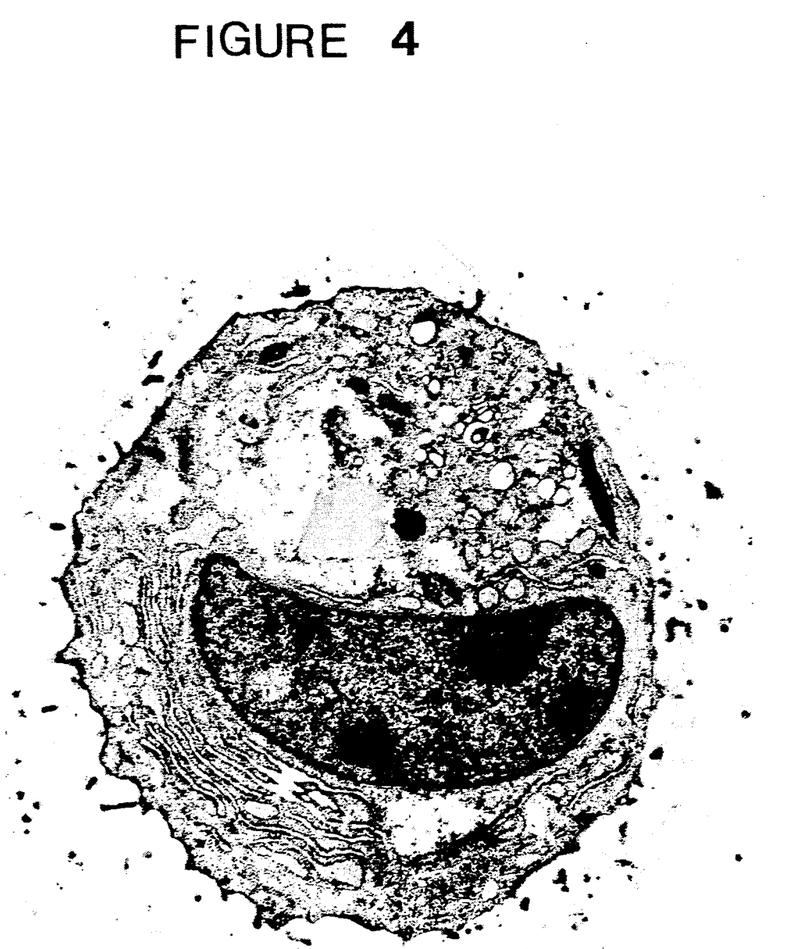
FIG. 4 is an electron micrograph of a chondrocyte surrounded by a pericellular matrix (→) and an interterritorial matrix within the cartilage tissue generated in culture on collagen-coated inserts.
Figure 5:
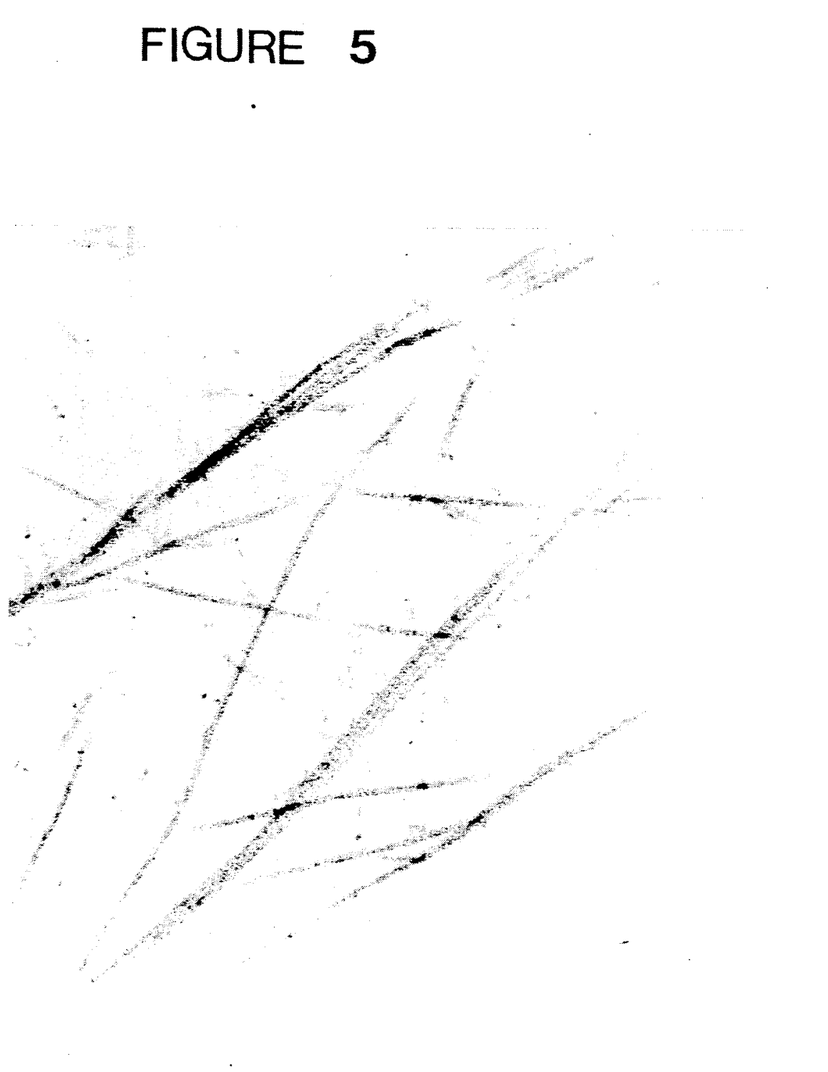
FIG. 5 is an electron micrograph of the interterritorial matrix of reconstituted cartilage tissue showing the presence of collagen fibers with characteristic periodic banding.

Examination by electron microscopy showed that the cultured tissue had a pericellular and interterritorial arrangement similar to that of bovine cartilage, as shown in FIG. 4. Chondrocytes with abundant rough endoplasmic reticulum were observed surrounded by matrix. The pericellular matrix contained numerous thin nonbanded collagen fibers. The collagen in the interterritorial matrix was less compacted and embedded in an electron translucent amorphous material similar to articular cartilage. FIG. 5 shows collagen fibers from the interterritorial matrix of reconstituted cartilage tissue. The collagen fibers exhibit the periodic banding characteristic of collagen fibers in the interterritorial zone of in vivo cartilage tissue. Numerous electron dense granules were present, which appeared as dots throughout the matrix, indicating the presence of proteoglycans.

EXAMPLE 2

In Vitro Synthesis of Type II Collagen

The presence of type II collagen in the cartilage tissue grown in vitro was measured to confirm that the cultured chondrocytes had maintained their differentiated phenotype.

Chondrocyte cultures were established, following the procedures outlined in Example 1 above, and maintained in culture for 2–4 weeks. The cartilage tissue was extracted with 100 μg/ml of pepsin at 4° C. After 24 hours an additional 100μg of pepsin was added and the extraction continued for another 24 hours. The pepsin extract was neutralized with the addition of an equal volume of Laemmli's buffer.

The presence of type II collagen was determined by polyacrylamide gel electrophoresis in the presence of sodium dodecylsulfate (SDS-PAGE) according to the procedure of Laemmli (U.K., Nature (London) 227, 680 (1974)). An 8% polyacrylamide gel was used. A sample of pepsin extract was applied to the gel and electrophoresed at 100 Ma for about 2 hours. Bands on the gel were visualized by staining with Coomassie Brilliant Blue. Only one band was observed co-migrating with the collagen standard. The identity of the band was confirmed by Western blot analysis to be type II collagen. The Western blot analysis was carried out by known standard techniques, generally as described in Coding, J.W., Monoclonal Antibodies: Principles and Practice, 2nd ed., Academic Press, London pp. 195–199, 1986. The band was transferred electrophoretically from the gel to nitrocellulose sheets and incubated with one of two antibodies directed against type II collagen or an antibody directed against type I collagen (Southern Biotechnology Assoc., U.S.A). One anti-type II collagen monoclonal antibody was obtained from Developmental Studies Hybridoma Bank, Iowa and one was a polyclonal antibody obtained from Southern Biotechnology Assoc. U.S.A. The blots were subjected to three washes and incubated for one hour in alkaline phosphatase conjugated to anti-IgG antibody. Blots were washed 3 times and developed with NBT/BCIP (Promega, U.S.A.) from 1 to 30 minutes, until colour developed.

Figure 6:
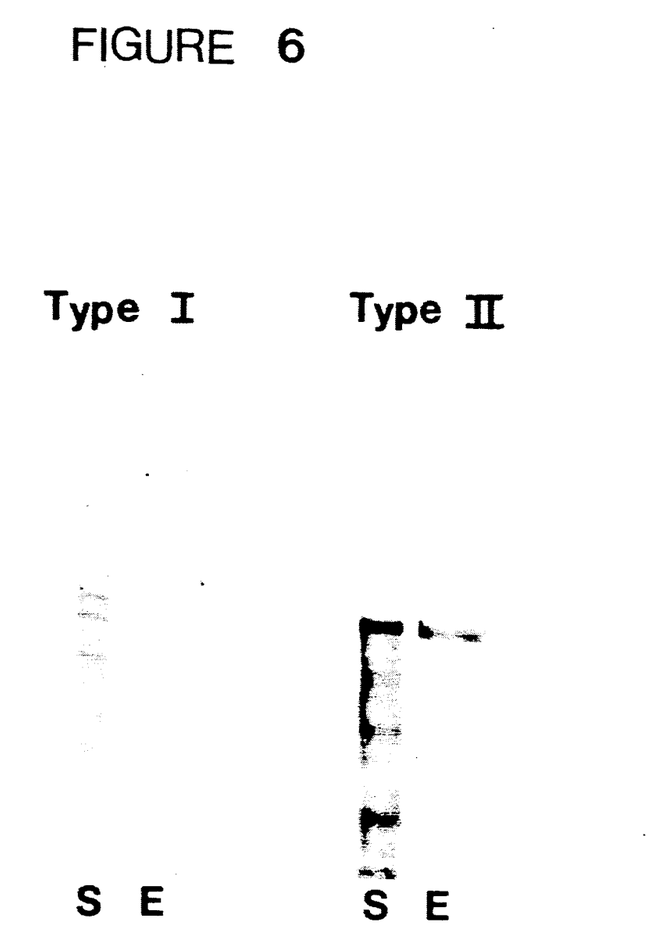
FIG. 6 is a Western blot showing the presence of Type II collagen in a pepsin extract (E) of the cartilage tissue generated in culture and a collagen standard (S)

Type II collagen was detected in the cultures as shown in FIG. 6. Only type II collagen was detected in the pepsin extract of the reconstituted cartilage tissue, as indicated by the arrow on FIG. 6. The results confirm that type II collagen is the major collagen produced by the chondrocyte culture.

Figure 7:
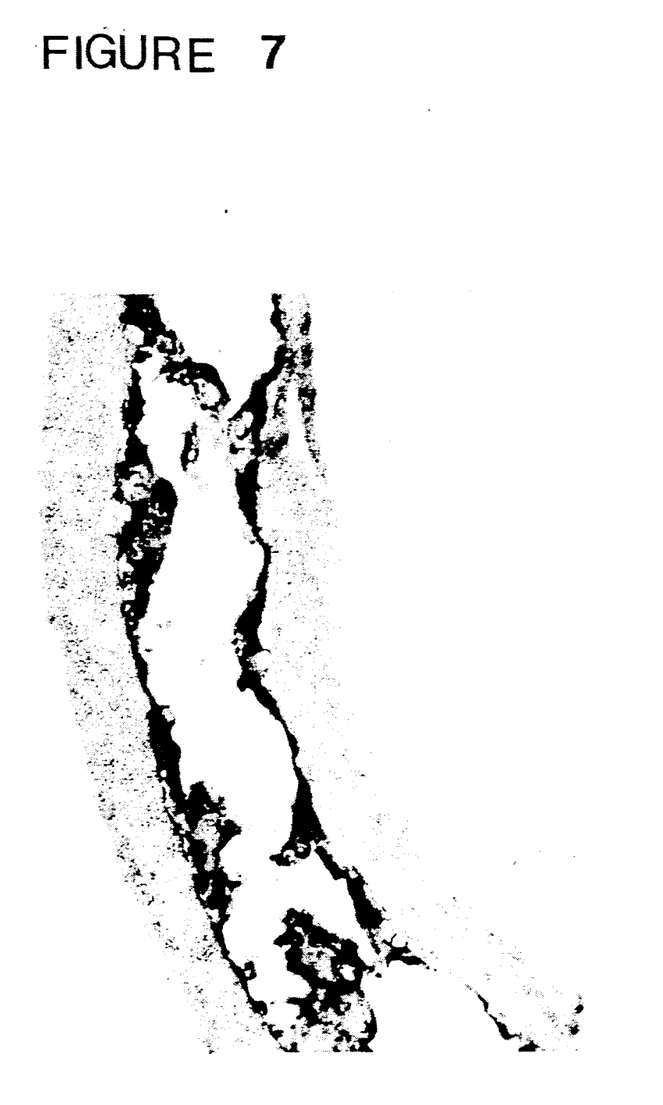
FIG. 7 is a photomicrograph of a section of reconstituted cartilage tissue incubated with anti-Type II collagen antibody, followed by anti-rabbit IgG conjugated to alkaline phosphate.
Figure 8:
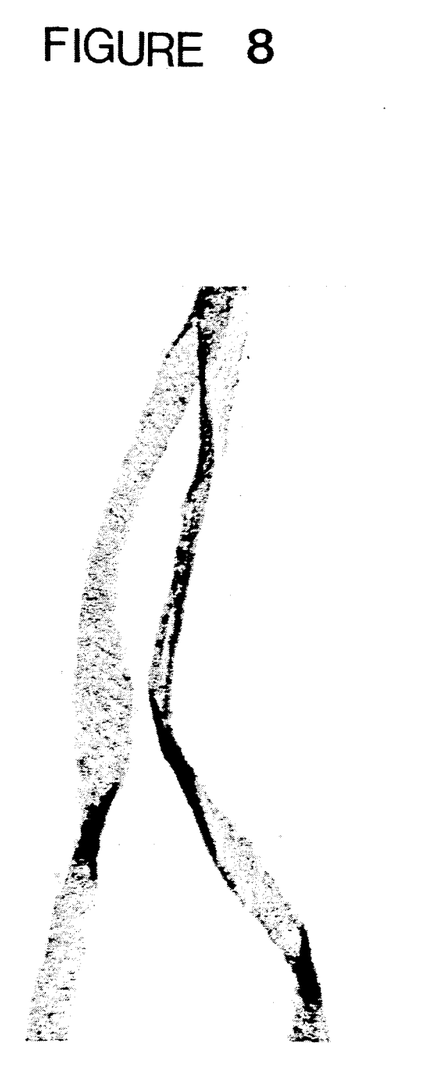
FIG. 8 is a photomicrograph of a section of reconstituted cartilage tissue incubated with antibody directed against Factor VIII related antigen and reacted as in FIG. 7.

The distribution of type II collagen in the chondrocyte cultures was examined as follows. Frozen sections of the cultured collagen tissue were predigested with 300 I.U. testicular hyaluronidase at 37° C. for 15 minutes. The sections were washed in phosphate buffered saline and incubated with polyclonal anti-type II collagen antibody (Southern Biotechnology Associates 1:100 dilution), for 3 hours at room temperature. The sections were washed in phosphate buffered saline and then incubated for 45 minutes with anti-rabbit IgG antibody conjugated to alkaline phosphate (Vector, U.S.A.). The sections were washed three times. 5-Bromo-4-chloro-3-indolyl phosphate nitroblue tetrazolium was added for substrate, and colour development. The sections were then counterstained with nuclear fast red stain, coverslipped and examined by light microscopy. The blue staining indicates the presence of Type II collagen throughout the cartilage, as shown in FIG. 7. Control sections were stained with antibody directed against Factor VIII related antigen, which is not present in cartilage. The cartilage matrix was unstained in the control sections, as shown in FIG. 8.

EXAMPLE 3

Interleukin 1 Stimulates Matrix Loss in the Chondrocyte Culture

Chondrocyte cultures were established as described above and grown for 2 weeks. The cultures were incubated with 10 ng/ml of human recombinant interleukin 1β (Ciba-Geigy, Switzerland) for seven days. After seven days the cultures were processed for light microscopy as described above in Example 1 and assessed histologically following staining with toluidine blue. Toluidine blue staining was taken as an indication of the presence of sulphated proteoglycans. Toluidine blue staining was greatly diminished in cultures treated with IL-1, compared to untreated controls, indicating a loss of cartilage and matrix components in the remaining cartilage.

EXAMPLE 4

Ratio of Galactosamine to Glucosamine

The ratio of galactosamine, which is present in chondroitin sulphate and dermatan sulphate, to glucosamine, which is present in hyaluronate and keratan sulphate, was determined in the insert cultures and compared to the ratios in bovine articular cartilage.

The tissue sample, comprising bovine articular cartilage or cultured cartilage tissue following papain digestion was hydrolysed with 6 N hydrochloric acid and examined by high pressure liquid chromatography using a Water's Pico Tag amino acid analysis system (Biotechnology Centre, University of Toronto) the ratio of galactosamine to glucosamine in the bovine articular cartilage was 5.55, whereas in the cultured cartilage, the ratio was 5.14. There was no significant difference between the ratios, indicating that the ratio of these glycosaminoglycans are likely similar in both the intact tissue and the artificial tissue generated in culture. The ratio of galactosamine to glucosamine is indicative of the types of glycosaminoglycans present in the extracellular matrix of the bovine cartilage and the cultured cartilage tissue.

I claim:

1. A biological material comprising cartilage tissue reconstituted on a substrate in vitro from isolated chondrocytes and characterized by a continuous layer of cartilage tissue, having a substantial extracellular matrix and comprising:

a superficial zone wherein chondrocytes are flattened and arranged parallel to the substrate;

mid and deep zones wherein the chondrocytes are spherical;

and wherein the matrix in the superficial, mid and deep zones contains collagen fibres.

2. A biological material as claimed in claim 1 wherein the substrate comprises a porous tissue culture insert coated with at least one attachment factor.

3. A biological material as claimed in claim 2 wherein the insert is a MILLICELL®-CM.

4. A biological material as claimed in claim 2 wherein at least one of the attachment factors is collagen.

5. A biological material as claimed in claim 4 wherein the collagen is type I or II collagen.

6. A biological material as claimed in claim 1, wherein the collagen is predominantly type II collagen.

7. A biological material as claimed in claim 1, wherein the cartilage tissue contains proteoglycans containing galactosamine and glucosamine having a ratio of galactosamine to glucosamine of 4.5 to 6.5.

8. A biological material as claimed in claim 1, further containing sulphated proteoglycans within the matrix.

9. A biological material as claimed in claim 8, wherein the sulphated proteoglycans increase in abundance from the superficial to the mid and deep zones.

10. A method for producing a biological material comprising reconstituted cartilage tissue comprising:

isolating chondrocytes from articular cartilage tissue;

forming a monolayer of chondrocytes on a substrate which is selected to permit growth media to be applied above and below the substrate;

culturing the chondrocytes on the substrate in growth media which is applied above and below the chondrocytes on the substrate to produce a biological material characterized by a continuous layer of cartilage tissue having a substantial extracellular matrix and comprising:

a superficial zone wherein chondrocytes are flattened and arranged parallel to the substrate; and mid and deep zones wherein the chondrocytes are spherical;

and wherein the matrix in the superficial, mid and deep zones contains collagen fibres.

11. A method as claimed in claim 10 wherein the chondrocytes are isolated from human articular cartilage tissue.

12. A method as claimed in claim 10 wherein the chondrocytes are isolated from bovine articular cartilage.

13. A method as claimed in claim 12, wherein the chondrocytes are isolated by sequential enzyme digestion techniques.

14. A method as claimed in claim 10 wherein the isolated chondrocytes are mesenchymal cells.

15. A method as claimed in claim 10 wherein the substrate is a porous tissue culture insert coated with at least one attachment factor.

16. A method as claimed in claim 15 wherein the porous tissue culture insert is MILLICELL®-CM.

17. A method as claimed in claim 15 wherein the attachment factors are selected from the group consisting of type I collagen, type II collagen, type IV collagen, fibronectin, gelatin, laminin, polylysine, vitronectin, cytotactin, echinonectin, entactin, tenascin, thrombospondin, uvomorulin, biglycan, chondroitin sulfate, decorin, dermatan sulfate, heparin, and hyaluronic acid.

18. A method as claimed in claim 15, wherein at least one of the attachment factors is type I collagen.

19. A method as claimed in claim 10, wherein the chondrocytes are cultured at a cell density of at least $0.1 \times 10^6/cm^2$.

20. A method as claimed in claim 10, wherein the chondrocytes are cultured at a cell density of 1.0 to $7 \times 10^6/cm^2$.

21. A method as claimed in claim 10, wherein the growth media is Ham's F12 medium.

22. A method as claimed in claim 10 wherein the chondrocytes are cultured for at least 14 days.

* * * * *

UNITED STATES PATENT AND TRADEMARK OFFICE
CERTIFICATE OF CORRECTION

PATENT NO. : 5,326,357
DATED : July 5, 1994
INVENTOR(S) : Rita A. Kandel

It is certified that error appears in the above-identified patent and that said Letters Patent is hereby corrected as shown below:

Title page, item [54] and in col. 1, line 2, replace Cartridge with --Cartilage--.

Signed and Sealed this

Twenty-fifth Day of July, 1995

Attest:

BRUCE LEHMAN

Attesting Officer     Commissioner of Patents and Trademarks